(12) United States Patent
Schmidt-Leithoff et al.

(10) Patent No.: US 7,973,198 B2
(45) Date of Patent: Jul. 5, 2011

(54) METHOD FOR SYNTHESIZING OPTICALLY ACTIVE CARBONYL COMPOUNDS

(75) Inventors: Joachim Schmidt-Leithoff, Freiburg (DE); Christoph Jäkel, Limburgerhof (DE); Rocco Paciello, Bad Dürkheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/597,025

(22) PCT Filed: Apr. 17, 2008

(86) PCT No.: PCT/EP2008/054644
§ 371 (c)(1),
(2), (4) Date: Oct. 22, 2009

(87) PCT Pub. No.: WO2008/132057
PCT Pub. Date: Nov. 6, 2008

(65) Prior Publication Data
US 2010/0152494 A1    Jun. 17, 2010

(30) Foreign Application Priority Data

Apr. 25, 2007  (EP) ..................................... 07106922

(51) Int. Cl.
*C07C 45/62*    (2006.01)
(52) U.S. Cl. .......................... 568/388; 568/396; 568/459
(58) Field of Classification Search .................. 568/388, 568/396, 459
See application file for complete search history.

(56) References Cited

U.S. PATENT DOCUMENTS

| 4,237,072 | A  | 12/1980 | Aviron-Violet et al. |
| 6,838,061 | B1 | 1/2005  | Berg et al. |
| 7,534,921 | B2 | 5/2009  | Jaekel et al. |
| 2008/0214877 | A1 | 9/2008 | Rauls et al. |
| 2008/0242893 | A1 | 10/2008 | Jaeckel et al. |

FOREIGN PATENT DOCUMENTS

| EP | 0000315 A1 | 1/1979 |
| EP | 1140349 A1 | 10/2001 |
| EP | 1225163 A2 | 7/2002 |
| JP | 5278812 A  | 2/1977 |
| JP | 52-078812 A | 7/1977 |
| WO | WO-2006/040096 A1 | 4/2006 |
| WO | WO 2007/012655 A1 | 2/2007 |
| WO | WO 2007/023109 A1 | 3/2007 |

OTHER PUBLICATIONS

Dang et al., "Catalyse D'Hydrogenation En Phase Homogene Des Aldehydes α-β Insatures. Application a la Synthese Asymetruque Du Citronellal", *Journal of Molecular Catalysis*, vol. 16, pp. 51-59 (1982).

Chapuis et al., "Synthesis of Citronellal by $Rh^1$-Catalysed Asymmetric Isomerization of N,N-Diethyl-Substituted Geranyl- and Nerylamines or Geraniol and Nerol in the Presence of Chiral Diphosphino Ligands, under Homogeneous and Supported Conditions", *Helvetica Chimica Acta*, vol. 84, pp. 230-242 (2001).

Trambouze et al., "Chemical Reactors From Design to Operation", Ed. TECHNIP, pp. 280-283 (2004).

Zehner et al., "Modelling Fluid Dynamics in Multiphase Reactors", *Chemical Engineering Science*, vol. 51, No. 10, pp. 1735-1744 (1996).

Tani et al., "Metal-assisted terpenoid synthesis. 7. Highly enantioselective isomerization of prochiral allylamines catalyzed by chiral diphosphine rhodium(I) complexes. Preparation of optically active enamines", *J. Am. Chem. Soc.*, vol. 106, No. 18, pp. 5208-5217 (1984).

Otsuka et al., "Catalytic Asymmetric Hydrogen Migration of Allylamines", *Synthesis*, pp. 665-680 (1991).

*Primary Examiner* — Sikarl A Witherspoon
(74) *Attorney, Agent, or Firm* — Connolly Bove Lodge & Hutz LLP

(57) ABSTRACT

The present invention relates to a process for preparing optically active carbonyl compounds by asymmetrically hydrogenating α,β-unsaturated carbonyl compounds in the presence of optically active transition metal catalysts which are soluble in the reaction mixture and have at least one carbon monoxide ligand, the optically active catalyst which has at least one carbon monoxide ligand and is to be used in each case being prepared by pretreating a catalyst precursor with a gas mixture comprising carbon monoxide and hydrogen and the asymmetric hydrogenation being performed in the presence of carbon monoxide supplied additionally to the reaction mixture.

19 Claims, No Drawings

METHOD FOR SYNTHESIZING OPTICALLY ACTIVE CARBONYL COMPOUNDS

RELATED APPLICATIONS

This application is a national stage application (under 35 U.S.C. §371) of PCT/EP2008/054644, filed Apr. 17, 2008, which claims benefit of European Application No. 07106922.3, filed Apr. 25, 2007.

The present invention relates to a process for preparing optically active carbonyl compounds by asymmetrically hydrogenating α,β-unsaturated carbonyl compounds in the presence of optically active transition metal catalysts which are soluble in the reaction mixture and have at least one carbon monoxide ligand. The present invention relates especially to a process for preparing optically active aldehydes or ketones, especially citronellal, by asymmetrically hydrogenating the corresponding optically active α,β-unsaturated aldehydes or ketones in the presence of carbon monoxide.

Many optically active aldehydes and ketones constitute valuable intermediates for the synthesis of highly upgraded chiral substances of value and active ingredients and are themselves often sought-after fragrances and aromas.

EP-A 0 000 315 relates to a process for preparing optically active citronellal by hydrogenating geranial or neral in the presence of a catalyst complex which is composed of rhodium and a chiral phosphine and is dissolved in the reaction system.

T.-P. Dang et al. describe, in J. Mol. Cat. 1982, 16, 51-59, the homogeneously catalyzed hydrogenation of α,β-unsaturated aldehydes and the application of the process to the preparation of optically active citronellal. The catalysts used were complexes composed of a rhodium carbonyl and a chiral diphosphine.

Chapuis et al., in Helv. Chim. Acta 2001, 84, 230-242, footnote 4, also mention the asymmetric hydrogenation of geranial or neral to optically active citronellal in the presence of a catalyst composed of $Rh_4(CO)_{12}$ and (R,R)-chiraphos ((2R,3R)-2,3-bis(diphenylphosphino)butane).

A problem in the case of performance of reactions catalyzed (homogeneously) by means of soluble catalysts consists in the often insufficient stability of the catalyst complexes used or of the catalytically active metal or transition metal complex which forms therefrom. Against the background of the often high price of such catalysts or catalyst precursors, homogeneously catalyzed reactions with complex transition metal catalysts are employable on the industrial scale in an economically viable manner only in specific cases.

JP-A 52078812 describes a process for hydrogenating α,β-unsaturated aldehydes such as crotonaldehyde, cinnamaldehyde or α-methylcinnamaldehyde over homogeneous Rh catalysts under hydroformylation conditions in the presence of a triarylphosphine, of a tertiary amine in a stoichiometric amount and of carbon monoxide.

WO 2006/040096 discloses a process for preparing optically active carbonyl compounds by asymmetrically hydrogenating α,β-unsaturated carbonyl compounds in the presence of optically active transition metal catalysts which are soluble in the reaction mixture and have at least one carbon monoxide ligand, which comprises pretreating the catalyst with a gas mixture comprising carbon monoxide and hydrogen and/or performing the asymmetric hydrogenation in the presence of carbon monoxide supplied additionally to the reaction mixture.

When the reaction is performed in such a way that the catalyst is pretreated with a gas mixture comprising carbon monoxide and hydrogen and the subsequent hydrogenation is performed in the presence of carbon monoxide supplied additionally to the reaction mixture, the carbon monoxide concentration of the reaction mixture during the hydrogenation is often difficult to control. In addition, the pretreatment is generally performed using significantly higher carbon monoxide concentrations than asymmetric hydrogenation, so that large amounts of carbon monoxide, which stem from the pretreatment of the catalyst, can be entrained into the hydrogenation and have a disadvantageous effect there.

It was accordingly an object of the present invention to improve the process disclosed in the aforementioned WO 2006/040096 to the effect that the pretreatment of the catalyst and the performance of the asymmetric hydrogenation can be performed in a simple manner from a process technology point of view at the carbon monoxide concentrations optimal in each case for the individual steps. Moreover, the improved process should enable the performance of the asymmetric hydrogenation at substantially constant carbon monoxide concentrations.

The object is achieved by providing a process for preparing optically active carbonyl compounds by asymmetrically hydrogenating α,β-unsaturated carbonyl compounds in the presence of optically active transition metal catalysts which are soluble in the reaction mixture and have at least one carbon monoxide ligand, the optically active catalyst which has at least one carbon monoxide ligand and is to be used in each case being prepared by pretreating a catalyst precursor with a gas mixture comprising carbon monoxide and hydrogen and the asymmetric hydrogenation being performed in the presence of carbon monoxide supplied additionally to the reaction mixture, which comprises a) performing the pretreatment of the catalyst precursor with a gas mixture comprising from 20 to 90% by volume of carbon monoxide, from 10 to 80% by volume of hydrogen and from 0 to 5% by volume of further gases, the proportions by volume mentioned adding up to 100% by volume, at a pressure of from 5 to 100 bar, b) removing excess carbon monoxide from the catalyst thus obtained before use in the asymmetric hydrogenation and c) performing the asymmetric hydrogenation in the presence of hydrogen with a carbon monoxide content of from 100 to 1200 ppm.

The process according to the invention is suitable for preparing optically active carbonyl compounds such as aldehydes, ketones, esters, lactones or lactams by asymmetrically, i.e. enantioselectively, hydrogenating the corresponding carbonyl compounds which have an ethylenic double bond in the α,β-position to the carbonyl group. According to the invention, the ethylenic double bond in the α,β-position to the carbonyl group is hydrogenated in the presence of an optically active transition metal catalyst which is soluble in the reaction mixture and has at least one carbon monoxide, i.e. CO, ligand to a carbon-carbon single bond, while the newly created tetrahedral carbon atom in the β-position is asymmetrically substituted and obtained in nonracemic form. In the context of the present invention, the term "asymmetric hydrogenation" is accordingly understood to mean a hydrogenation in which the two enantiomeric forms of the hydrogenation product are not obtained in equal parts.

To prepare the optically active catalyst which has at least one carbon monoxide ligand and is to be used in each case, a pretreatment of a catalyst precursor with a gas mixture comprising carbon monoxide and hydrogen is performed. The inventive asymmetric hydrogenation is performed in the presence of carbon monoxide supplied additionally to the reaction mixture.

The process according to the invention comprises performing the pretreatment of the catalyst precursor mentioned with a gas mixture comprising from 20 to 90% by volume of carbon monoxide, from 10 to 80% by volume of hydrogen and from 0 to 5% by volume of further gases, the proportions by volume mentioned adding up to 100% by volume, at a pressure of from 5 to 100 bar, removing excess carbon monoxide from the catalyst thus obtained before use in the asymmetric hydrogenation and performing the asymmetric hydrogenation in the presence of hydrogen with a carbon monoxide content of from 100 to 1200 ppm.

The transition metal catalysts which are soluble in the reaction mixture and are to be used in accordance with the invention have at least one CO ligand at least in a form which is passed through in the catalytic cycle or in a form which precedes the actual catalytic cycle, but it is unimportant whether this catalyst form having at least one CO ligand constitutes the actual catalytically active catalyst form. In the process according to the invention, the catalyst form having at least one CO ligand is stabilized in an advantageous manner by the carbon monoxide supplied additionally to the reaction mixture.

The process according to the invention is particularly suitable for preparing optically active carbonyl compounds of the formula (I)

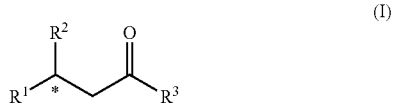

(I)

where the $R^1$, $R^2$ radicals are each an unbranched, branched or cyclic alkyl radical which has from 1 to 25 carbon atoms and may optionally bear one or more, generally from 1 to about 5, preferably from 1 to 3, more preferably 1 or 2, ethylenic double bonds and/or one or more, generally from 1 to about 5, preferably from 1 to 3, more preferably 1 or 2, identical or different substituents selected from the group of the substituents $OR^4$, $NR^5R^6$, halogen, $C_6$-$C_{10}$-aryl and $C_3$-$C_9$-hetaryl, and which, together with $R^3$, may form a 5- to 25-membered ring, with the proviso that $R^1$ and $R^2$ are different, the $R^3$ radical is hydrogen or an unbranched, branched or cyclic alkyl radical which has from 1 to 25 carbon atoms and may optionally bear one or more, generally from 1 to about 5, preferably from 1 to 3, more preferably 1 or 2, ethylenic double bonds and/or one or more, generally from 1 to about 5, preferably from 1 to 3, more preferably 1 or 2, identical or different substituents selected from the group of the substituents $OR^4$, $NR^5R^6$, halogen, $C_6$-$C_{10}$-aryl and $C_3$-$C_9$-hetaryl, or is $OR^7$ or $NR^8R^9$, where $R^4$, $R^5$, $R^6$ are each independently hydrogen, $C_1$-$C_6$-alkyl, $C_6$-$C_{10}$-aryl, $C_7$-$C_{12}$-aralkyl or $C_7$-$C_{12}$-alkylaryl and $R^5$ and $R^6$ together may also be an alkylene chain which has from 2 to 5 carbon atoms and may be interrupted by N or O and $R^7$ is an unbranched, branched or cyclic alkyl radical which has from 1 to 25 carbon atoms and may optionally bear one or more ethylenic double bonds and one or more identical or different substituents selected from the group of the substituents $OR^4$, $NR^5R^6$, halogen, $C_6$-$C_{10}$-aryl and $C_3$-$C_9$-hetaryl, and, together with $R^1$ or $R^2$, may form a 5- to 25-membered ring and $R^8$ is an unbranched, branched or cyclic alkyl radical which has from 1 to 25 carbon atoms and may optionally bear one or more, preferably from 1 to 3, more preferably 1 or 2, ethylenic double bonds and one or more, preferably from 1 to 3, more preferably 1 or 2, identical or different substituents selected from the group of the substituents $OR^4$, $NR^5R^6$, halogen, $C_6$-$C_{10}$-aryl and $C_3$-$C_9$-hetaryl, and, together with $R^1$, $R^2$ or $R^9$, may form a 5- to 25-membered ring and $R^9$ is hydrogen, $C_1$-$C_6$-alkyl, $C_6$-$C_{10}$-aryl, $C_7$-$C_{12}$-aralkyl or $C_7$-$C_{12}$-alkylaryl, or, together with $R^8$, may form a 5- to 25-membered ring and

* designates an asymmetric carbon atom, by asymmetrically hydrogenating α,β-unsaturated aldehydes or ketones of the formula (II)

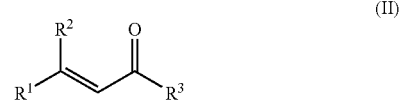

(II)

where the $R^1$ to $R^3$ radicals are each as defined above.

In the context of the present invention, the following definitions are specified by way of example for substituents or radicals mentioned:

$C_1$-$C_6$-Alkyl is, for example, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl.

$C_6$-$C_{10}$-Aryl is, for example, phenyl or naphthyl.

$C_7$-$C_{12}$-Aralkyl is, for example, phenylmethyl, 1-phenylethyl, 2-phenylethyl, 1-phenylpropyl, 2-phenylpropyl or 3-phenylpropyl.

$C_3$-$C_9$-Hetaryl is, for example, 2-furyl, 3-furyl, 2-pyrroyl, 3-pyrroyl, 2-thienyl, 3-thienyl, 2-pyridyl, 3-pyridyl, 4-pyridyl, 2-indolyl, 3-indolyl, 4-indolyl, 5-indolyl, 6-indolyl, 7-indolyl.

$C_7$-$C_{12}$-Alkylaryl is, for example, 1-methylphenyl, 2-methylphenyl, 3-methylphenyl, 1-ethylphenyl, 2-ethylphenyl, 3-ethylphenyl, 1-propylphenyl, 2-propylphenyl, 3-propylphenyl, 1-isopropylphenyl, 2-isopropylphenyl, 3-isopropylphenyl, 1-butylphenyl, 2-butylphenyl, 3-butylphenyl, 1-isobutylphenyl, 2-isobutylphenyl, 3-isobutylphenyl, 1-sec-butylphenyl, 2-sec-butylphenyl, 3-sec-butylphenyl, 1-tert-butylphenyl, 2-tert-butylphenyl, 3-tert-butylphenyl, 1-(1-pentenyl)phenyl, 2-(1-pentenyl)phenyl, 3-(1-pentenyl)phenyl, 1-(2-pentenyl)phenyl, 2-(2-pentenyl)phenyl, 3-(2-pentenyl)phenyl, 1-(3-pentenyl)phenyl, 2-(3-pentenyl)phenyl, 3-(3-pentenyl)phenyl, 1-(1-(2-methylbutyl))phenyl, 2-(1-(2-methylbutyl))phenyl, 3-(1-(2-methylbutyl))phenyl, 1-(2-(2-methylbutyl))phenyl, 2-(2-(2-methylbutyl))phenyl, 3-(2-(2-methylbutyl))phenyl, 1-(3-(2-methylbutyl))phenyl, 2-(3-(2-methylbutyl))phenyl, 3-(3-(2-methylbutyl))phenyl, 1-(4-(2-methylbutyl))phenyl, 2-(4-(2-methylbutyl))phenyl, 3-(4-(2-methylbutyl))phenyl, 1-(1-(2,2-dimethylpropyl)) phenyl, 2-(1-(2,2-dimethylpropyl))phenyl, 3-(1-(2,2-dimethylpropyl))phenyl, 1-(1-hexenyl)phenyl, 2-(1-hexenyl)phenyl, 3-(1-hexenyl)phenyl, 1-(2-hexenyl)phenyl, 2-(2- hexenyl)phenyl, 3-(2-hexenyl)phenyl, 1-(3-hexenyl)phenyl, 2-(3-hexenyl)phenyl, 3-(3-hexenyl)phenyl, 1-(1-(2-methylpentenyl))phenyl, 2-(1-(2-methylpentenyl))phenyl, 3-(1-(2-methylpentenyl))phenyl, 1-(2-(2-methylpentenyl))phenyl, 2-(2-(2-methylpentenyl))phenyl, 3-(2-(2-methylpentenyl))phenyl, 1-(3-(2-methylpentenyl))phenyl, 2-(3-(2-methylpentenyl))phenyl, 3-(3-(2-methylpentenyl))phenyl, 1-(4-(2-methylpentenyl))phenyl, 2-(4-(2-methylpentenyl))phenyl, 3-(4-(2-methylpentenyl))phenyl, 1-(5-(2-methylpentenyl))phenyl, 2-(5-(2-methylpentenyl))phenyl, 3-(5-(2-methylpentenyl))phenyl, 1-(1-(2,2-dimethylbutenyl))phenyl, 2-(1-(2,2-dimethylbutenyl))phenyl, 3-(1-(2,2-dimethylbutenyl))phenyl, 1-(3-(2,2-dimethylbutenyl))phenyl, 2-(3-(2,2-dimethylbutenyl))phenyl, 3-(3-(2,2-dimethylbutenyl))phenyl, 1-(4-(2,2-dimethylbutenyl))phenyl, 2-(4-(2,2-dimethylbutenyl))phenyl, 3-(4-(2,2-dimethylbutenyl))phenyl.

In the context of the present invention, halogen refers to fluorine, chlorine, bromine or iodine, preferably fluorine, chlorine or bromine.

The process according to the invention is accordingly suitable, for example, for preparing the following compounds of the formulae (I-1) to (I-25) specified by way of example in optically active form:

(I-1)

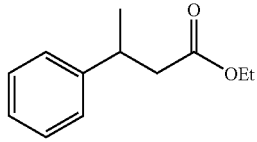

(I-2)

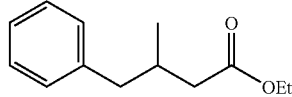

(I-3)

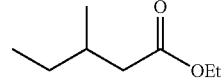

(I-4)

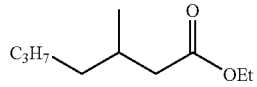

(I-5)

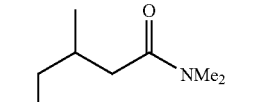

(I-6)

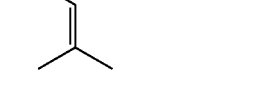

(I-7)

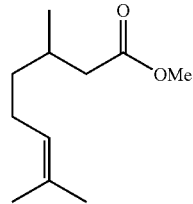

(I-8)

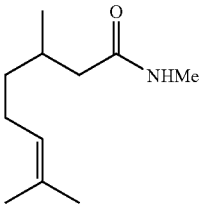

(I-9)

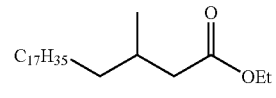

(I-10)

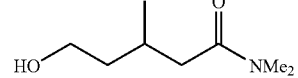

(I-11)

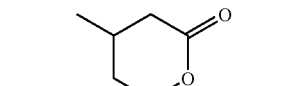

(I-12)

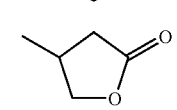

(I-13)

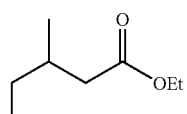

(I-14)

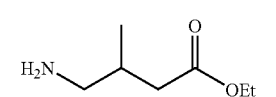

(I-15)

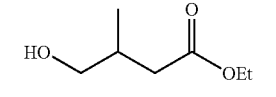

(I-16)

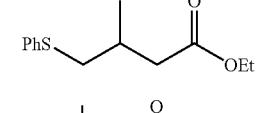

(I-17)

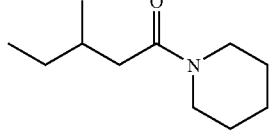

(I-18) 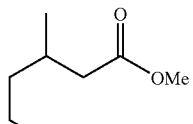

(I-19) 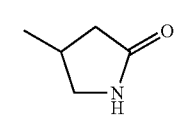

(I-20) 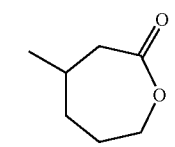

(I-21) 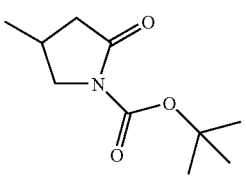

(I-22) 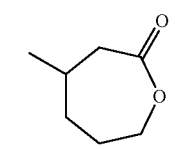

(I-23) 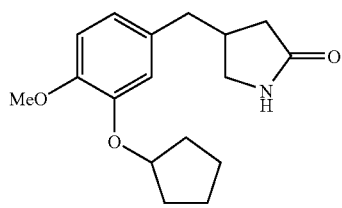

(I-24) 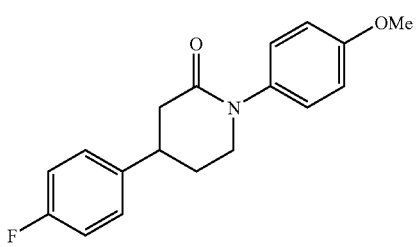

(I-25) 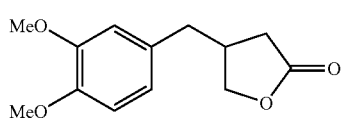

The process according to the invention is especially suitable for preparing optically active aldehydes or ketones by asymmetrically hydrogenating α,β-unsaturated aldehydes or ketones. Accordingly, it is especially suitable for preparing optically active compounds of the formula (I')

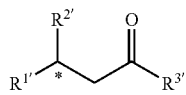
(I')

in which $R^{1'}$, $R^{2'}$ may each be as defined above for $R^1$ and $R^2$ and $R^{3'}$ is hydrogen or an unbranched, branched or cyclic alkyl radical which has from 1 to 25 carbon atoms and may optionally bear one or more, generally from 1 to about 5, preferably from 1 to 3, more preferably 1 or 2, ethylenic double bonds and/or one or more, generally from 1 to about 5, preferably from 1 to 3, more preferably 1 or 2, identical or different substituents selected from the group of the $OR^4$, $NR^5R^6$, halogen, $C_6$-$C_{10}$-aryl and $C_3$-$C_9$-hetaryl substituents, and may, together with $R^{1'}$ or $R^{2'}$, form a 5- to 25-membered ring, where $R^4$, $R^5$ and $R^6$ may each be as defined above, by asymmetrically hydrogenating α,β-unsaturated aldehydes or ketones of the formula (II')

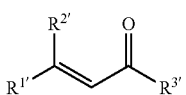
(II')

where the $R^{1'}$ to $R^{3'}$ radicals are each as defined above.

The process according to the invention is preferentially suitable for preparing optically active aldehydes of the formula (III) which have a methyl group in the β-position relative to the carbonyl group

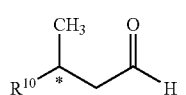
(III)

where $R^{10}$ is an unbranched or branched alkyl radical which has from 2 to 25 carbon atoms and may optionally have from 1 to 5, preferably from 1 to 3, more preferably 1 or 2, ethylenic double bonds and

* indicates an asymmetric carbon atom, by asymmetrically hydrogenating α,β-unsaturated aldehydes of the formula (IV) or (V)

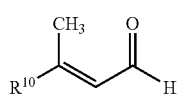
(IV)

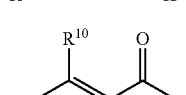
(V)

where the $R^{10}$ radical is as defined above.

Examples of aldehydes or ketones of the formulae (I') or (III) which can be prepared in optically active form in accordance with the invention include the following compounds:

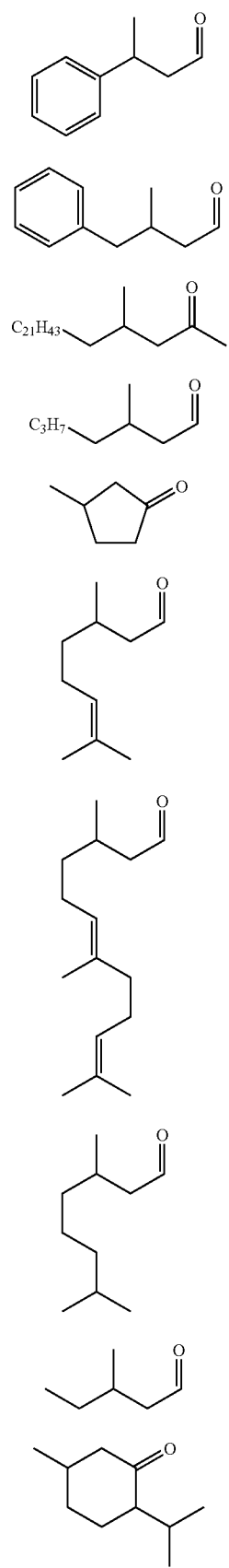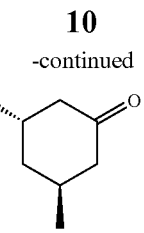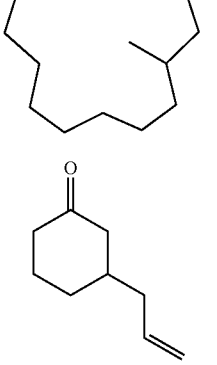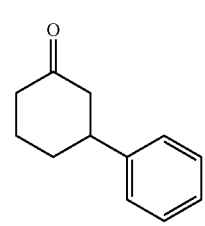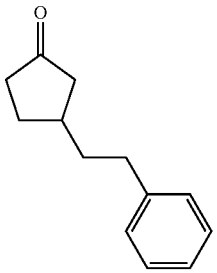

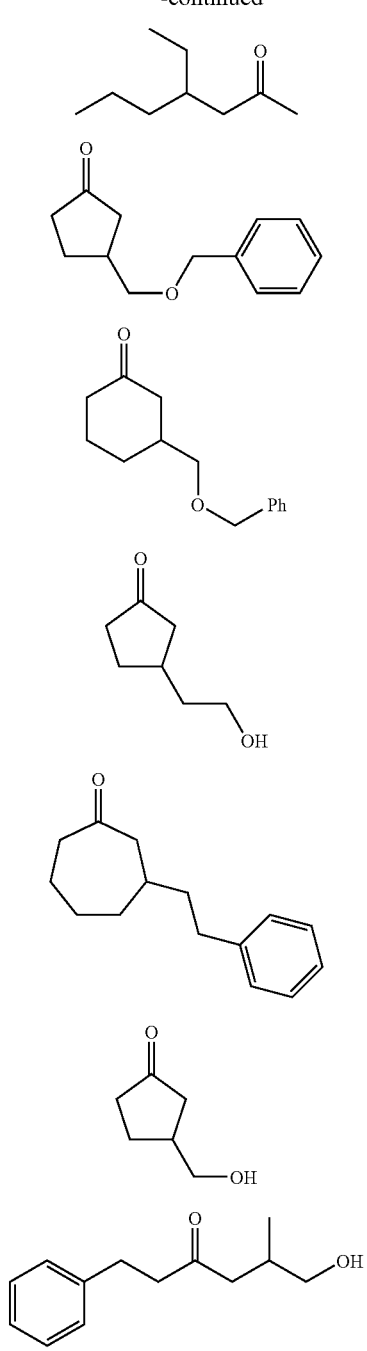

mentioned substrate or product classes. In principle, it is also possible to convert mixtures of the two double bond isomers in the inventive manner. In this way, mixtures of the two enantiomers of the desired target compound are obtained.

The process according to the invention is more preferentially suitable for preparing optically active citronellal of the formula (VI)

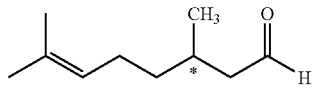

by asymmetrically hydrogenating neral of the formula (VII) or geranial of the formula (VIII)

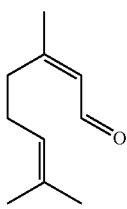

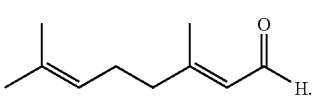

It is also possible to convert mixtures of geranial and neral in the inventive manner, in which case, as described above, mixtures of D- and L-citronellal are present and are optically active if the two enantiomers are not present therein in equal parts.

Especially preferred in the process according to the invention is the inventive preparation of D-citronellal by asymmetric hydrogenation of neral or geranial.

The inventive preparation process is carried out in the presence of an optically active transition metal catalyst which is soluble in the reaction mixture and has at least one carbon monoxide ligand.

Such catalysts are, for example, obtainable by reaction of at least one suitable transition metal compound which is soluble in the reaction mixture with an optically active ligand which has at least one phosphorus and/or arsenic atom.

Preferred transition metal compounds are those of the metals of transition group VIII of the Periodic Table of the Elements, in particular Ru, Rh, Pd, Ir and Pt. Transition metals of transition group VIII of the Periodic Table which are particularly preferred in accordance with the invention are Rh and Ir.

Suitable compounds of the transition metals mentioned are in particular those which are soluble in the selected reaction medium, for example salts or complexes with suitable ligands, for example carbonyl, acetylacetonate, hydroxyl, cyclooctadiene, norbornadiene, cyclooctene, methoxy, acetyl or other aliphatic or aromatic carboxylates. Transition metal compounds which are preferred in the process according to the invention are Rh(I) and Rh(III) and Rh(0) compounds, Ir(I), Ir(III), Ir(IV) and Ir(0) compounds, Ru(II), Ru(III), Ru(IV) and Ru(0) compounds, Pd(II), Pd(IV) and Pd(0) compounds and Pt(II), Pt(IV) and Pt(0) compounds. Preference is given to those transition metal compounds which already have at least one CO ligand. In addition, it is also possible to use transition metal compounds which do not have any CO According to the invention, the aldehydes of the formula (III) are accessible by asymmetrically, i.e. enantioselectively, hydrogenating the corresponding α,β-unsaturated aldehydes of the formulae (IV) or (V). The compounds of the formulae (IV) and (V) constitute Ea-double bond isomers of one another. In principle, the optically active aldehydes of the formula (III) are accessible starting from both double bond isomers of the formulae (IV) and (V). Depending on the selection of the enantiomeric form of the catalyst, i.e. depending on the selection of the (+)- or (−)-enantiomer of the catalyst and of the (+)- or (−)-enantiomer of the chiral ligand used, one of the enantiomers of the optically active aldehyde is obtained preferentially in the inventive manner from the E- or Z-double bond isomer used. The same applies to the aforeligands in the process according to the invention as a starting compound for preparing the catalysts to be used in accordance with the invention. Under the conditions of the preformation which can optionally be carried out in accordance with the invention or the inventive hydrogenation conditions, these are converted to the desired catalysts with addition of carbon monoxide.

Examples of transition metal compounds which can be used in accordance with the invention are: $RhCl_3$, $Rh_2(OAc)_4$, $[Rh(cod)Cl]_2$, $Rh(CO)_2acac$, $[Rh(cod)OH]_2$, $[Rh(cod)OMe]_2$, $Rh_4(CO)_{12}$, $Rh_6(CO)_{16}$ or $Ir_4(CO)_{12}$, $[Ir(cod)Cl]_2$, where "acac" is an acetylacetonate ligand and "cod" is a cyclooctadiene ligand.

The transition metal compounds and complexes mentioned and further examples thereof are known and are adequately described in the literature or may be prepared by those skilled in the art analogously to the compounds already known.

According to the invention, the transition metal compounds mentioned are used typically in an amount of from about 0.01 to about 1 mol %, preferably of from about 0.05 to about 0.5 mol %, in particular of from about 0.02 to about 0.2 mol % (based on the transition metal atoms present) in relation to the amount of substrate to be hydrogenated.

In the case of reactions carried out under continuous conditions, the ratio of amount of transition metal compound used as a precursor of the inventive homogeneous catalyst to the amount of substrate to be hydrogenated is advantageously selected in such a way that a catalyst concentration in the range of from about 100 ppm to 10 000 ppm, in particular in the range of from about 200 ppm to 5000 ppm, is maintained.

According to the invention, the transition metal compounds mentioned are contacted with a further compound which is optically active, preferably substantially enantiomerically pure (i.e. has an enantiomeric excess of at least about 99%) and has at least one phosphorus and/or arsenic atom, preferably at least one phosphorus atom. This compound, to be referred to as a chiral ligand, forms the transition metal catalyst to be used in accordance with the invention in the reaction mixture, or in the preformation mixture with the transition metal compound used.

Special preference is given to those chiral ligands which have two phosphorus atoms and form chelate complexes with the transition metal used.

Suitable chiral ligands in the context of the present invention are those compounds as described, for example, in: I. Ojima (ed.), *Catalytic Asymmetric Synthesis*, Wiley-VCh, 2nd edition, 2000 or in E. N. Jacobsen, A. Pfaltz, H. Yamamoto (eds.), *Comprehensive Asymmetric Catalysis*, 2000, Springer, or in W. Tang, X. Zhang, *Chem. Rev* 2003, 103, 3029-3069.

The following compounds are listed by way of example as chiral ligands which can be used with preference in accordance with the invention:

(1)

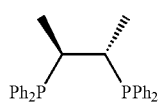

(2)

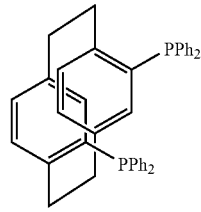

(3)

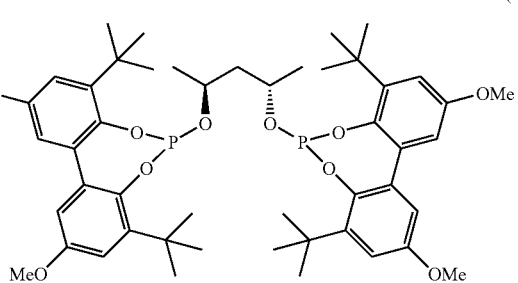

(4)

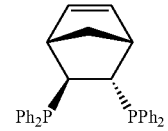

(5)

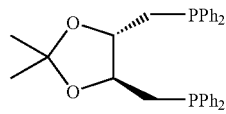

(6)

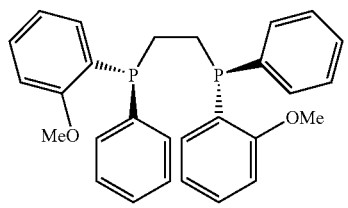

(7)

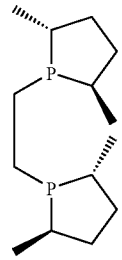

(8)

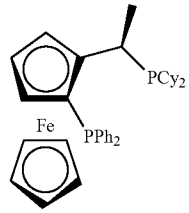

(9)

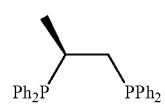

(10)
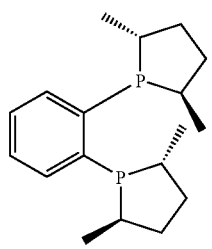
(11)
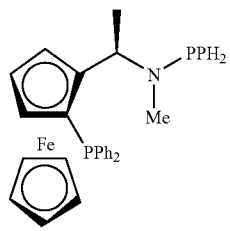
(12)
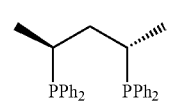
(13)
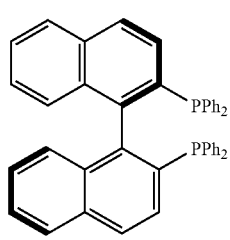
Additionally listed by way of example as chiral ligands which can be used in accordance with the invention are the following compounds:
(14)
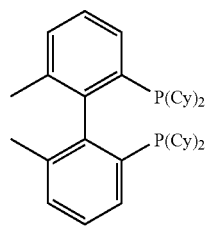
(15)
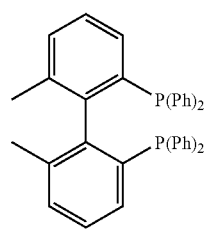
(16)
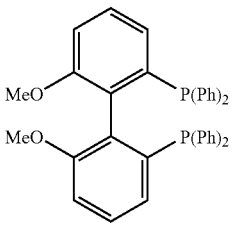
(17)
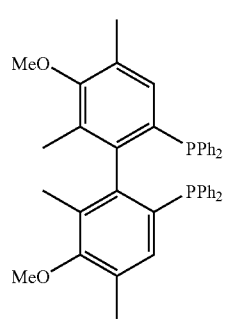
(18)
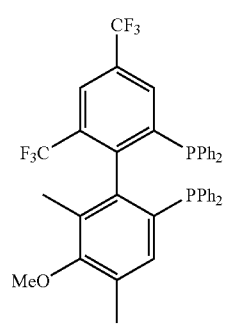
(19)
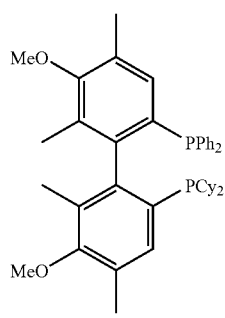
(20)
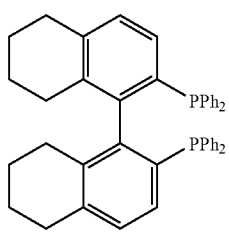

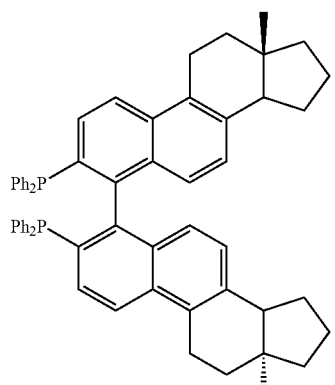
(21)
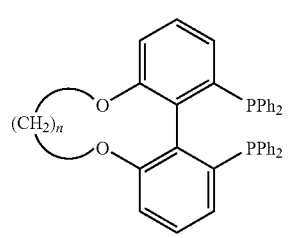
n = 1-6
(22)
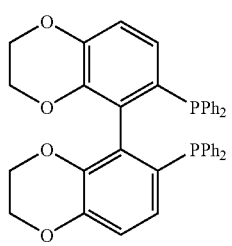
(23)
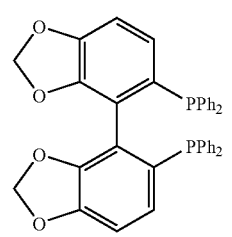
(24)
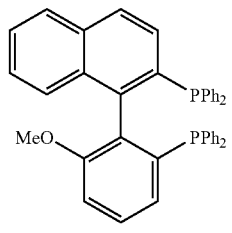
(25)
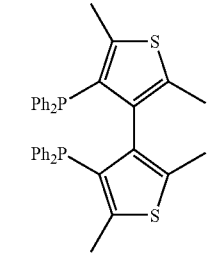
(26)
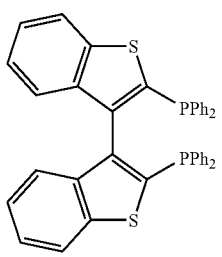
(27)
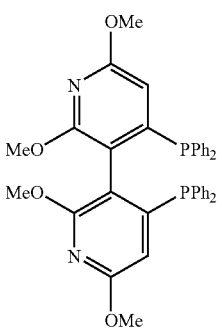
(28)
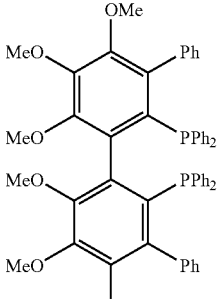
(29)
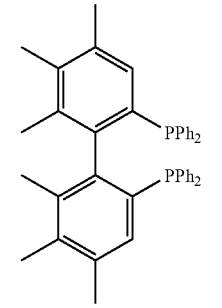
(31)
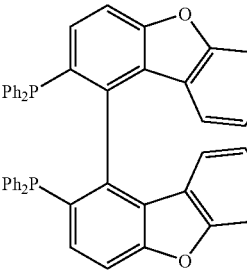
(32)

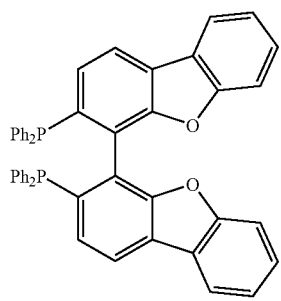
(33)
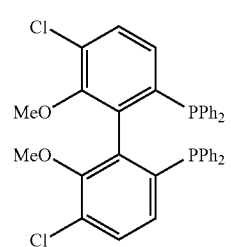
(34)
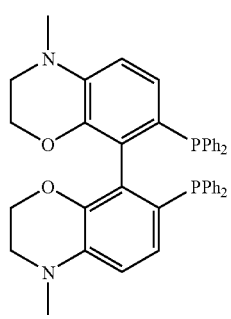
(35)
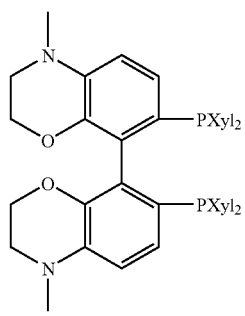
(36)
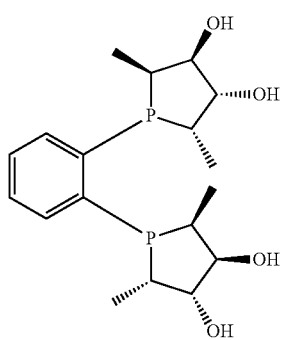
(37)
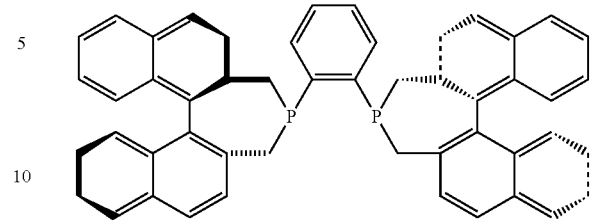
(38)
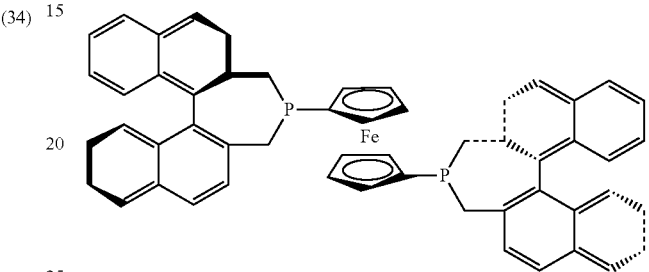
(39)
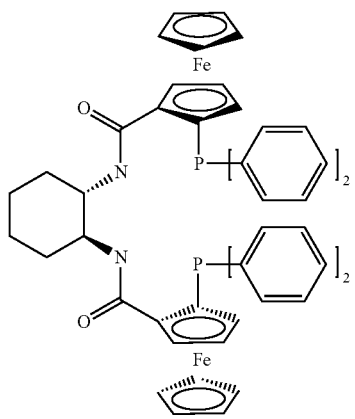
(40)
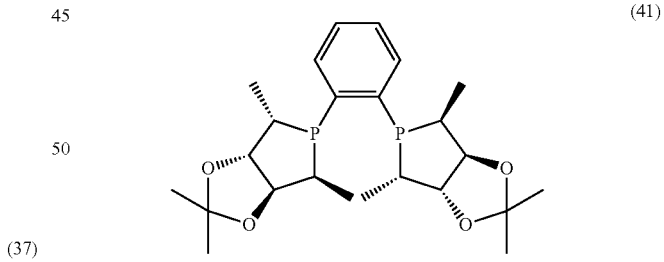
(41)
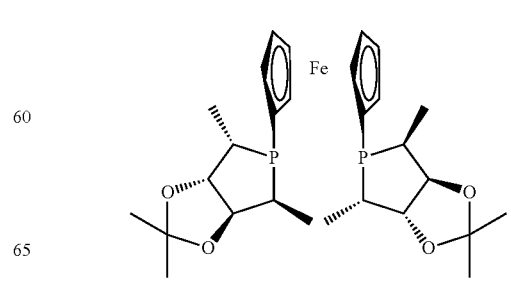
(42)

-continued
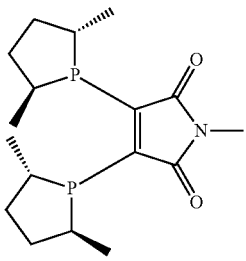
(43)
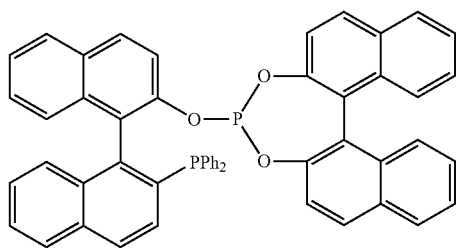
(44)
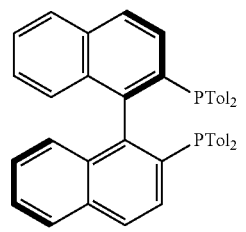
(45)
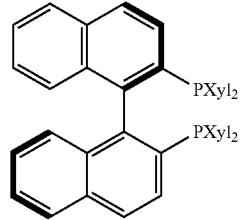
(46)
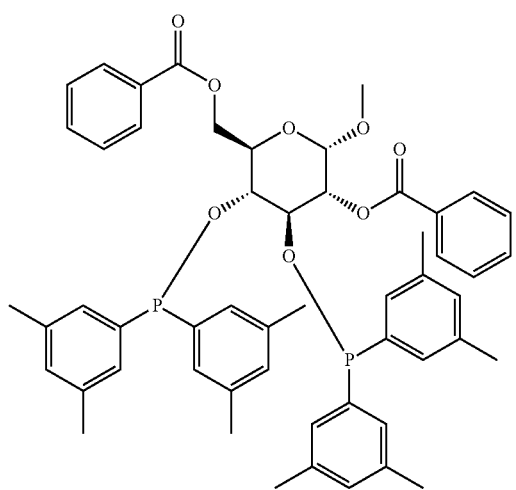
(47)
-continued
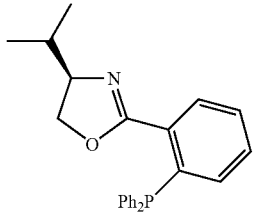
(48)
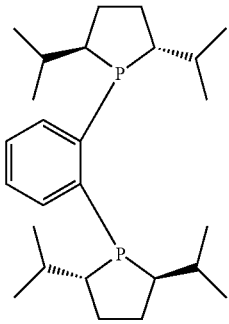
(49)
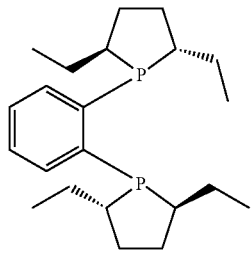
(50)
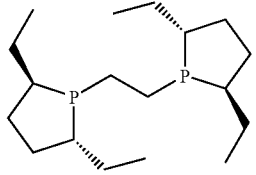
(51)
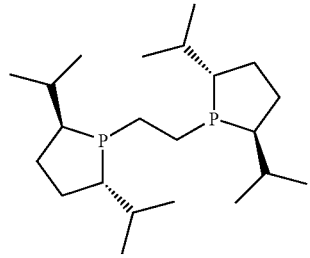
(52)
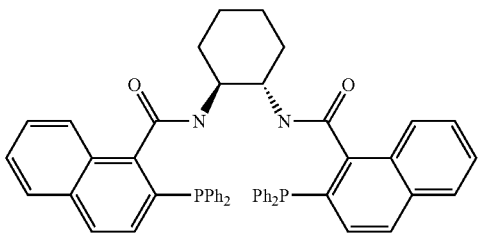
(53)

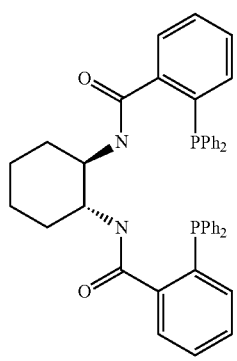
(54)
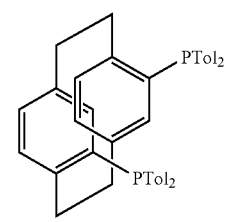
(55)
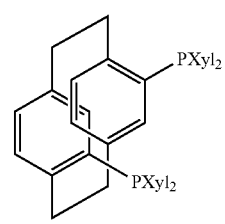
(56)
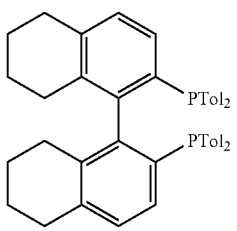
(57)
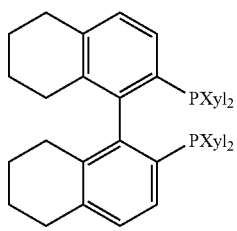
(58)
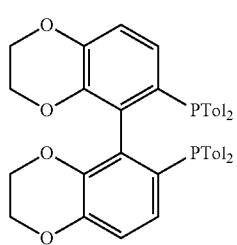
(59)
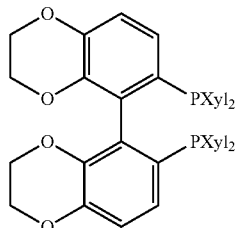
(60)
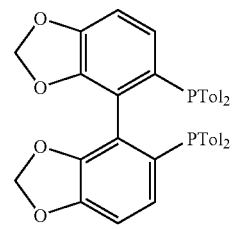
(61)
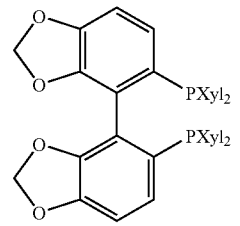
(62)
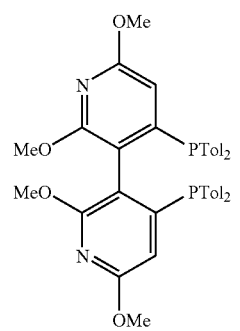
(63)
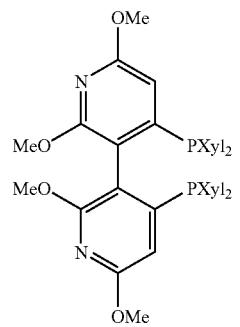
(64)
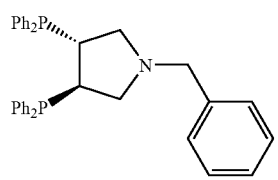
(65)

-continued
(66)
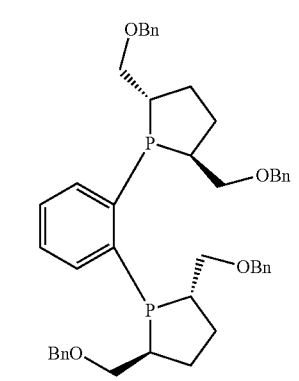
(67)
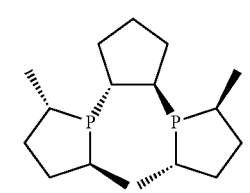
(68)
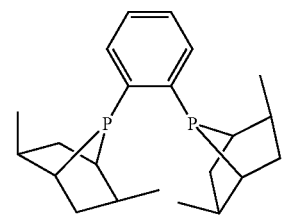
(69)
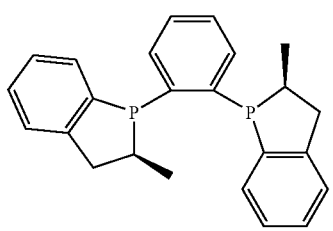
(70)
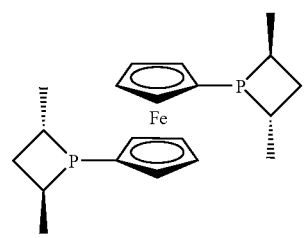
(71)
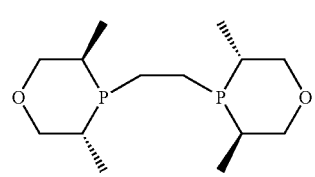
(72)
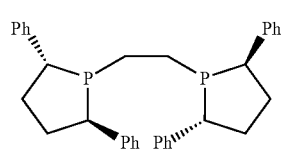
-continued
(73)
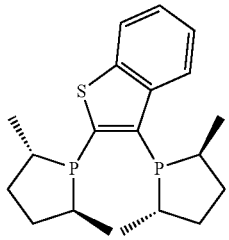
(74)
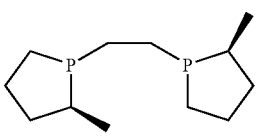
(75)
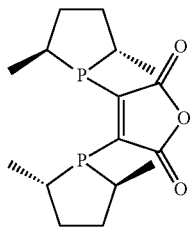
(76)
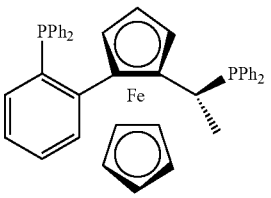
(77)
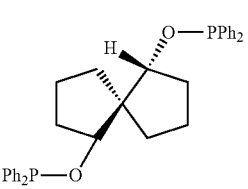
(78)
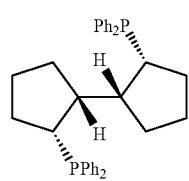
(79)
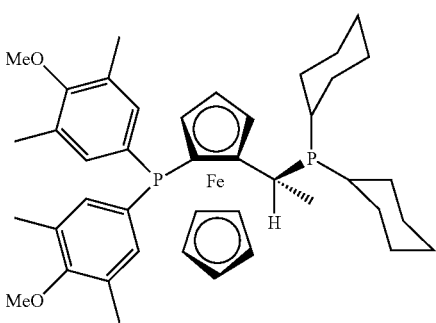

-continued
(80) 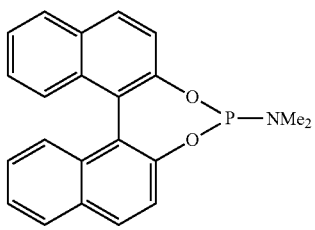
(81) 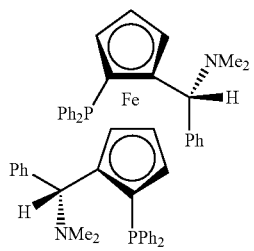
(82) 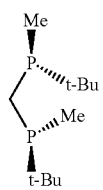
(83) 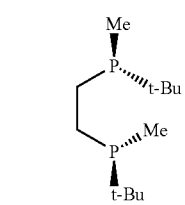
(84) 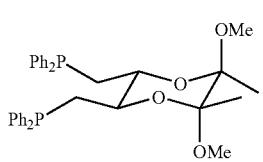
(85) 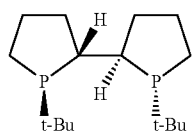
(86) 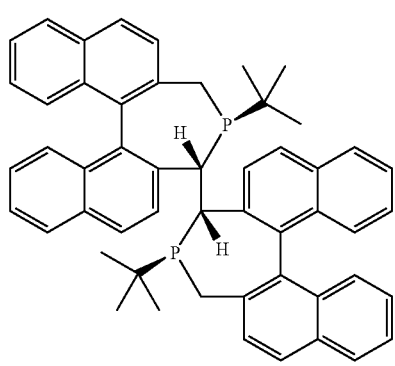
-continued
(87) 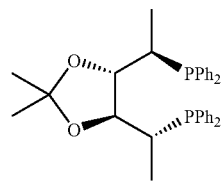
(88) 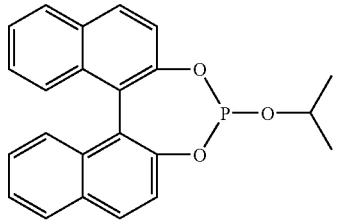
(89) 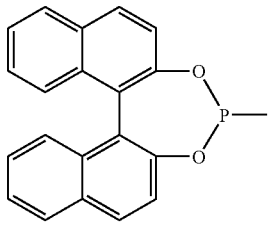
(90) 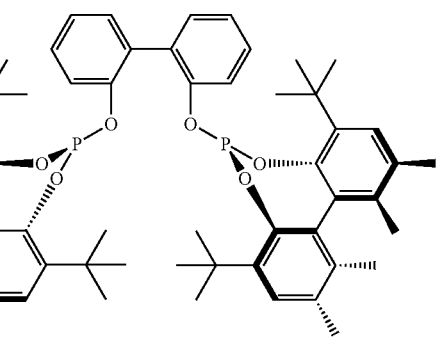
In these structures, "Ph" means phenyl, "Cy" means cyclohexyl, "Xyl" means xylyl, "Tol" means p-tolyl and "Bn" means benzyl.
Ligands which are particularly preferred in accordance with the invention are those of the structural formulae (1) to (13) and (37), (38), (41), (43), (49), (50), (51), (52), (65), (66), (67), (68), (69), (71), (72), (73), (74), (75), (83), (84), (85), (86), (87).
Especially preferred ligands are those of the general formulae (IX) to (XI)
(IX) 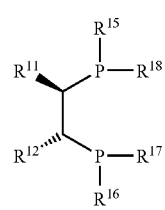

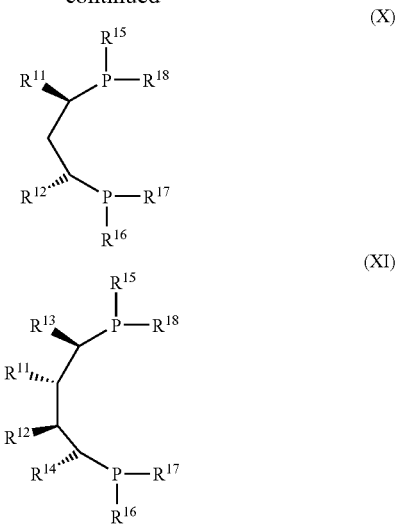

in which

R[11], R[12]: are each independently an unbranched, branched or cyclic alkyl radical which has from 1 to 20 carbon atoms and may optionally bear one or more, generally from 1 to about 4, ethylenic double bonds and/or one or more, generally from 1 to about 4, identical or different substituents selected from the group of the $OR^{19}$, $NR^{20}R^{21}$, halogen, $C_6$-$C_{10}$-aryl and $C_3$-$C_9$-hetaryl substituents, and R[11] and R[12] together may form a 4- to 20-membered ring which may contain one or more, generally 1 or 2, oxygen atoms, and R[13], R[14]: are each independently hydrogen or straight-chain or branched $C_1$- to $C_4$-alkyl, and R[15], R[16], R[17], R[18]: are each $C_6$- to $C_{10}$-aryl, each of which may optionally bear one or more, generally from 1 to 8, preferably from 1 to 4, substituents selected from the group of the $C_1$- to $C_4$-alkyl, $C_6$- to $C_{10}$-aryl, $C_1$- to $C_4$-alkoxy and amino substituents, and R[19], R[20], R[21]: are each independently hydrogen, $C_1$-$C_4$-alkyl, $C_6$-$C_{10}$-aryl, $C_7$-$C_{12}$-aralkyl or $C_7$-$C_{12}$-alkylaryl, where R[20], R[21]: together may also be an alkylene chain which has from 2 to 5 carbon atoms and may be interrupted by N or O.

Ligands especially preferred in the process according to the invention are those of the general formula (IX), especially the compounds of the formula (I) referred to hereinafter as "chiraphos".

According to the invention, the chiral ligands selected may each be used in the form of their two enantiomers. A ligand very particularly preferred in accordance with the invention is (R,R)-chiraphos (ent-(1)).

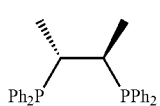

ent-(1)

In the case of use of chiral ligands with two phosphorus atoms, they are advantageously used in an amount of from about 1 to about 10 mol, preferably from about 1 to about 4 mol, most preferably from 1 to 2 mol, per molar equivalent of metal which is present in the transition metal compound used.

The actual precatalysts comprising at least one carbon monoxide ligand can be obtained from the selected transition metal compound and the selected chiral ligand by combination and subsequent pretreatment as described below with a mixture of hydrogen and carbon monoxide.

To prepare the optically active catalyst which has at least one carbon monoxide ligand and is to be used in each case, in step a) of the process according to the invention, a catalyst precursor is pretreated with a gas mixture comprising from 20 to 90% by volume of carbon monoxide, from 10 to 80% by volume of hydrogen and from 0 to 5% by volume of further gases, where the proportions by volume mentioned add up to 100% by volume, at a pressure of from 5 to 100 bar. This pretreatment is also referred to hereinafter, as within the entire present invention, as preformation.

The term "catalyst precursor" is understood to mean those compounds which are obtainable by contacting or by reaction of at least one transition metal compound soluble in the reaction mixture as specified above with an optically active ligand which has at least one phosphorus and/or arsenic atom as specified above.

To perform the preformation, the selected transition metal compound and the selected chiral ligand and, if desired, the substrate to be hydrogenated asymmetrically are typically dissolved in a suitable solvent or solution medium which is inert under the reaction conditions, for example ether, tetrahydrofuran, toluene, chlorobenzene, octadecanol, biphenyl ether, Texanol, Marlotherm®, Oxooel 9N (hydroformylation products formed from isomeric octenes, BASF Aktiengesellschaft) and the like. The solution medium used may also be the substrate to be converted, the product or any high-boiling by-products which occur in the reaction. A gas mixture comprising hydrogen and carbon monoxide as described above is injected into the resulting solution, advantageously in a suitable pressure reactor or autoclave, at a pressure in the range from 5 to 100 bar (absolute), preferably at a pressure of from 10 to 100 bar, more preferably at a pressure of from 20 to 95 bar and especially preferably at a pressure of from 50 to 90 bar (in each case absolute).

In a preferred embodiment of the process according to the invention, the preformation in step a) is performed with a gas mixture comprising from 30 to 70% by volume of carbon monoxide, from 30 to 70% by volume of hydrogen and from 0 to 5% by volume of further gases, where the proportions by volume add up to 100% by volume, most preferably with a gas mixture comprising from 30 to 80% by volume of carbon monoxide, from 40 to 70% by volume of hydrogen and from 0 to 5% by volume of further gases and especially preferably with a gas mixture comprising from 40 to 60% by volume of carbon monoxide, from 40 to 60% by volume of hydrogen and from 0 to 5% by volume of further gases, where the proportions by volume mentioned in each case add up to 100% by volume.

A gas mixture especially preferred for the preformation is so-called synthesis gas, which consists typically of carbon monoxide to an extent of from about 35 to 55% by volume and from about 45 to 65% by volume of hydrogen, with or without traces of further gases.

The inventive preformation of the catalyst is performed typically at temperatures of from about 25° C. to about 100° C., preferably at from about 40° C. to about 80° C., more preferably at 50-70° C. When the preformation is performed in the presence of the substrate to be hydrogenated asymmetrically, the temperature is advantageously selected such that there is no troublesome degree of isomerization of the double bond to be hydrogenated. The preformation is complete typically after from about 1 to about 24 h, often after from about 1 to about 12 h.

After the preformation of the transition metal catalyst to be used or precursor thereof, in step b) of the process according to the invention, excess carbon monoxide is removed from the catalyst obtained by preformation or pretreatment with the gas mixture mentioned before it is used in the asymmetric hydrogenation.

The term "excess carbon monoxide" is understood to mean carbon monoxide which is present in gaseous or dissolved form in the reaction mixture obtained by preformation in step a) and is not bound to the transition metal catalyst or precursor thereof. Accordingly, the excess carbon monoxide not bound to the catalyst is removed at least substantially, i.e. to such a degree that any residual amounts of dissolved carbon monoxide do not become noticeably troublesome in the hydrogenation which follows. This is typically ensured when about 90%, preferably about 95% or more, of the carbon monoxide used for the preformation is removed in step b) of the process according to the invention. In step b) of the process according to the invention, preference is given to removing excess carbon monoxide completely from the catalyst obtained by preformation.

The excess carbon monoxide can be removed from the catalyst obtained in step a) or from the catalyst-comprising reaction mixture in step b) of the process according to the invention in various ways. Preference is given to decompressing the catalyst or the catalyst-comprising mixture obtained by preformation in step a) to a pressure of up to about 5 bar (absolute), preferably, especially, carrying out the preformation at a pressure in the range from 5 to 10 bar, to a pressure of less than 5 bar(absolute), preferably to a pressure in the range from about 1 bar to about 5 bar, preferably 1 to less than 5 bar, more preferably to a pressure in the range from 1 to 3 bar, even more preferably to a pressure in the range from about 1 to about 2 bar, especially preferably to standard pressure, such that gaseous, unbound carbon monoxide escapes from the product of the preformation.

The aforementioned decompression of the preformed catalyst can be effected, for example, using a high-pressure separator as known per se to those skilled in the art. Such separators in which the liquid is in the continuous phase are, for example, described in: Perry's Chemical Engineers' Handbook, 1997, 7th ed., McGraw-Hill, p. 14.95 and 14.96; the prevention of possible droplet entrainment is described on pages 14.87 to 14.90. The preformed catalyst can be decompressed in one or two stages until the desired pressure in the range from 1 bar to about 5 bar is attained, in the course of which the temperature falls typically to from 10 to 40° C.

Alternatively, the removal of excess carbon monoxide in step b) can also be achieved by so-called stripping of the catalyst or of the catalyst-comprising mixture with a gas, advantageously with a gas inert under the reaction conditions. The term "stripping" is understood by the person skilled in the art to mean the introduction of a gas into the catalyst or the catalyst-comprising reaction mixture, as described, for example, in W. R. A. Vauck, H. A. Müller, Grundoperationen chemischer Verfahrenstechnik [Basic Operations in Chemical Process Technology], Deutscher Verlag für Grundstoffchemie Leipzig, Stuttgart, 10th edition, 1984, page 800. Examples of suitable inert gases for this purpose include: hydrogen, helium, neon, argon, xenon, nitrogen and/or $CO_2$, preferably hydrogen, nitrogen, argon.

After the preformation in step a) and the freeing of the catalyst of excess carbon monoxide in step b), the asymmetric hydrogenation of the selected substrate in the presence of hydrogen with a carbon monoxide content of from 100 to 1200 ppm is performed in step c) of the process according to the invention.

The addition of additional carbon monoxide to the reaction mixture of the asymmetric hydrogenation can be undertaken in various ways: for example, the carbon monoxide can be added to the hydrogen used for the asymmetric hydrogenation or else be metered directly into the reaction solution in gaseous form. An example of a further possibility consists in adding compounds which readily release carbon monoxide, for example formates or oxalyl compounds, to the reaction mixture.

The proportion of carbon monoxide in the hydrogen used is, in a preferred embodiment of the process according to the invention, from about 300 to 1000 ppm, more preferably from 400 to 800 ppm.

The inventive asymmetric hydrogenation is advantageously undertaken at a pressure of from about 1 to about 300 bar, preferably from about 10 to about 100 bar, especially at from about 50 to about 100 bar, more preferably at about 60 to about 100 bar and a temperature of generally from about 0° C. to about 100° C., preferably from about 0° C. to about 30° C., especially at from about 10° C. to about 30° C.

The selection of the solvent to be used to perform the inventive asymmetric hydrogenation is not critical. Suitable solvents are, for example, those specified for the performance of the inventive preformation. Particularly advantageously, the asymmetric hydrogenation is performed in the same solvent as any preformation performed beforehand.

Suitable reaction vessels for performing the inventive asymmetric hydrogenation are in principle all of those which allow the reactions under the conditions specified, especially pressure and temperature, and are suitable for hydrogenation reactions, for example autoclaves, tubular reactors, bubble columns, etc.

When the hydrogenation in step c) of the process according to the invention is performed using high-boiling, generally viscous solvents, as described, for example, above for use in the pretreatment of the catalyst in step a) of the process according to the invention (for instance the octadecanol, biphenyl ether, Texanol, Marlotherm, Oxooel 9N solvents mentioned), or the hydrogenation is performed without additional use of solvents but with accumulation of the high boilers which form to a small degree as by-products (for example dimers or trimers which form through reactions of the reactants or products and subsequent conversion reactions), it may be advantageous to ensure good gas introduction and good mixing of gas phase and condensed phase. This is possible, for example, by performing the hydrogenation step of the process according to the invention in a gas circulation reactor. Gas circulation reactors are known per se to those skilled in the art and are described, for example, in P. Trambouze, J.-P. Euzen, Chemical Reactors, Ed. Technip, 2004, p. 280-283 and P. Zehner, R. Benfer, Chem. Eng. Sci. 1996, 51, 1735-1744, and also, for example, in EP 1 140 349.

In the case of use of a gas circulation reactor as specified above, it has been found to be particularly advantageous to introduce the gas or gas mixture (the carbon monoxide-comprising hydrogen) to be used into the gas circulation reactor in parallel to the reactants introduced into the reactor and/or to the circulating reaction mixture or to the catalyst by means of a simple nozzle or a two-substance nozzle. In this context, the two-substance nozzle is notable in that liquid and gas to be introduced into the reactor pass through two separate internal tubes under pressure to the nozzle mouth and are combined with one another there.

The process according to the invention can be performed with good success with and without addition of tertiary amines. Preference is given to performing the process according to the invention in the absence, i.e. without addition, of additional tertiary amines or in the presence only of catalytic amounts of additional tertiary amines. The amount of amine used may be between 0.5 and 500 molar equivalents based on the amount of metal used, but preferably from 1 to 100 molar equivalents based on the amount of metal used. The selection of the tertiary amine is not critical. In addition to short-chain alkylamines, for example triethylamine, it is also possible to use long-chain alkylamines, for example tridodecylamine. In a preferred embodiment, the hydrogenation process according to the invention is performed in the presence of a tertiary amine, preferably tridodecylamine, in an amount of from about 2 to 30 molar equivalents, preferably from about 5 to 20 molar equivalents and more preferably from 5 to 15 molar equivalents based on the amount of transition metal used.

Advantageously, the reaction is terminated when the target compound is present in the reaction mixture in the desired yield and the desired optical activity, i.e. with the desired enantiomeric excess (ee), as can be determined by the person skilled in the art by routine analyses, for example by means of chromatographic methods. Typically, the hydrogenation is complete after from about 1 to about 150 h, often after from about 2 to about 24 h.

The process according to the invention succeeds in providing optically active carbonyl compounds, especially optically active aldehydes, in high yields and enantiomeric excesses. Typically, the desired asymmetrically hydrogenated compounds are obtained in an enantiomeric excess of at least 80% ee, often with an enantiomeric excess of from about 85 to about 99% ee. It should be noted that the maximum achievable enantiomeric excess can depend on the purity of the substrate used, especially with regard to the isomeric purity of the double bond to be hydrogenated.

Accordingly, suitable starting substances are especially those which have an isomer ratio of at least about 90:10, preferably at least about 95:5, based on the E/Z double bond isomers.

The process according to the invention is notable in that the homogeneous catalysts used are stabilized by the carbon monoxide additionally introduced into the reaction system, which firstly significantly increases the lifetime of the catalysts and secondly enables the reusability of the homogeneous catalysts.

For example, the resulting reaction product can be removed from the reaction mixture by processes known per se to those skilled in the art, for example by distillation, for example by means of a fine-film evaporator, Sambays or the like, and the remaining catalyst, if appropriate after repeated preformation as described above, can be utilized in further reactions.

The process according to the invention can accordingly be performed either batchwise, semicontinuously or continuously and is suitable especially for reactions on the industrial scale. Preference is given to performing the process continuously.

The pretreatment of the catalyst precursor (preformation) to be performed in accordance with the invention in step a) and the actual asymmetric hydrogenation in step c) are advantageously performed in separate reaction vessels. When the preformed catalyst is transferred to the actual hydrogenation reactor, for example the gas circulation reactor as described above, the excess carbon monoxide can then be removed from the catalyst, for example by releasing the pressure employed for the preformation.

The hydrogenation can also be effected in a plurality of, preferably in two or three, more preferably in two, hydrogenation reactors connected in series. It is possible to use different or identical reactor types. In a preferred embodiment, the asymmetric hydrogenation is performed, for example, in a battery of two gas circulation reactors, in which case one functions as the main reactor and the second as the postreactor. To transfer the reaction mixture from the main reactor to the postreactor, it is possible, for example, to utilize a pressure gradient to be thus established if desired.

In a particularly preferred embodiment of the process according to the invention, neral or geranial, preferably neral, which comprises up to about 5 mol %, preferably up to about 2 mol %, of the particular double bond isomer is converted to optically active citronellal. To form the catalyst, preference is given to using a compound of rhodium soluble in the reaction mixture, especially $Rh_4(OAc)_4$, $[Rh(cod)Cl]_2$, $Rh(CO)_2acac$, $[Rh(cod)OH]_2$, $[Rh(cod)OMe]_2$, $Rh_4(CO)_{12}$ or $Rh_6(CO)_{16}$, and, as the chiral ligand, (R,R)-chiraphos or (S,S)-chiraphos ((2R,3R)-(+)-2,3-bis(diphenylphosphino)butane or (2S,3S)-(−)-2,3-bis(diphenylphosphino)butane) in a molar ratio of from about 1:1 to about 1:4 based on rhodium. In an especially preferred embodiment of the process according to the invention, neral which comprises up to about 5 mol %, preferably up to about 2 mol %, is converted to D-citronellal in the presence of $Rh(OAc)_3$, $[Rh(cod)Cl]_2$, $Rh(CO)_2acac$, $[Rh(cod)OH]_2$, $[Rh(cod)OMe]_2$, $Rh_4(CO)_{12}$ or $Rh_6(CO)_{16}$ and (R,R)-chiraphos.

In the preferred embodiment of the process according to the invention, the addition of solvents is dispensed with and the reactions mentioned are performed in the substrate to be converted or the product and if appropriate in high-boiling by-products as a solution medium. Especially preferred is the continuous reaction with reuse or recycling of the homogeneous catalyst stabilized in accordance with the invention.

A further aspect of the present invention relates to a process for preparing optically active menthol using optically active citronellal prepared by the process according to the invention. The preparation of optically active menthol proceeding from optically active citronellal is known. A key step here is the cyclization of optically active citronellal to optically active isopulegol as described, for example, in EP-A 1 225 163.

The optically active citronellal prepared in accordance with the invention can, as shown below schematically for the preparation of L-menthol of the formula (XIII), be cyclized to L-isopulegol of the formula (XII) in the presence of a suitable acid, especially of a Lewis acid, and then hydrogenated to L-menthol by processes known to those skilled in the art, for example by catalytic hydrogenation as described, for example, in J. Am. Chem. Soc. 1984, 106, 5208-5217 or Synthesis 1991, 665-680.

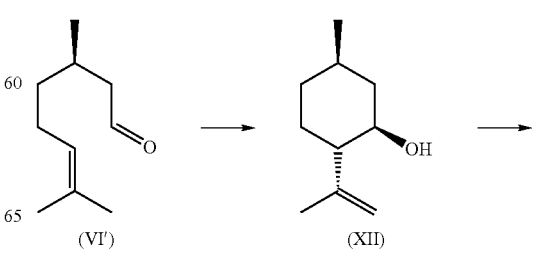

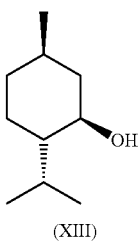

(XIII)

A further aspect of the present invention accordingly relates to a process for preparing optically active menthol, comprising the steps of
i) preparing optically active citronellal in the above-described process according to the invention,
ii) cyclizing the optically active citronellal thus prepared to optically active isopulegol in the presence of a Lewis acid and
iii) hydrogenating the optically active isopulegol thus prepared to optically active menthol.

In a preferred embodiment of this kind, R-citronellal is prepared in step i) by inventive hydrogenation of geranial or neral, preferably neral, the R-citronellal thus obtained is cyclized in step ii) to L-isopulegol, and the L-isopulegol thus obtained is hydrogenated in step iii) to L-menthol.

The examples which follow serve to illustrate the invention without restricting it in any way:

EXAMPLE 1

Continuous Asymmetric Hydrogenation of Cis-Citral with Controlled Reduction in the CO Content after the Preformation A continuous system was charged with a solution of a total of 10.4 g of $Rh(CO)_2acac$ and a total of 34.5 g of (R,R)-chiraphos in toluene (660 ml). The gas mixture was adjusted to a ratio of hydrogen to carbon monoxide ($H_2$:CO) of 1:1 in the preformation reactor at a pressure of 80 bar and a temperature of 60° C. The effluent of the preformation reactor was decompressed to standard pressure in a high-pressure separator and then compressed to 80 bar in the hydrogenation reactor. In the hydrogenation reactor, 158 l (STP)/h of $H_2$ (with 400 ppm of CO) were introduced at 20° C., such that a CO value of 550 ppm was established in the offgas of the hydrogenation reactor.

At a feed rate of 100 g/h of cis-citral (neral) with a content of 98% by weight, a product-containing fraction was distilled off continuously under reduced pressure such that the system contents remained virtually constant. With these settings, 110.9 mol (17.1 kg) of D-citronellal were isolated within 8 days. The yield of D-citronellal was 93% based on the cis-citral used.

COMPARATIVE EXAMPLE

Continuous Asymmetric Hydrogenation of Cis-Citral at Reduced CO Concentration in the Preformation and without Reduction of the Co Content after the Preformation A continuous system was charged with a solution of a total of 10.4 g of $Rh(CO)_2acac$ and a total of 34.5 g of (R,R)-chiraphos in toluene (660 ml). The gas mixture in the preformation reactor was adjusted to a ratio of 90:10 $H_2$:CO (35.1 l (STP)/h) at a pressure of 105 bar and a temperature of 60° C. The effluent of the preformation reactor was decompressed directly to 80 bar in the hydrogenation reactor without preceding decompression. In the hydrogenation reactor, 150 l (STP)/h of $H_2$ were introduced at 20° C., such that a CO value of about 800 ppm was established in the offgas of the hydrogenation reactor.

At a feed rate of 77 g/h of cis-citral (neral) with a content of 98% by weight, a product-containing fraction was distilled off continuously under reduced pressure such that the system contents remained virtually constant. With these settings, 82.1 mol of D-citronellal were isolated within 8 days.

The yield of D-citronellal was only 86% based on the cis-citral used.

EXAMPLE 2

Continuous Asymmetric Hydrogenation of Cis-Citral with Elevated CO Content in the Hydrogenation Reactor A continuous system was charged with a solution of a total of 10.4 g of $Rh(CO)_2acac$ and a total of 25.8 g of (R,R)-chiraphos in toluene (about 600 ml).

The ratio of hydrogen to carbon monoxide ($H_2$:CO) was adjusted to 1:1 in the preformation reactor at a pressure of 80 bar and a temperature of 60° C. The effluent of the preformation reactor was decompressed to standard pressure in a high-pressure separator and then compressed to 80 bar in the hydrogenation reactor. 60 l (STP)/h of $H_2$ (with 245 ppm of CO) were introduced into the hydrogenation reactor at 20° C. such that a CO value of about 600 ppm was established in the offgas of the hydrogenation reactor.

At a feed rate of 100 g/h of cis-citral (neral) with a content of 98% by weight, a product-containing fraction was distilled off continuously under reduced pressure such that the system contents remained virtually constant. With these settings, 2.88 mol (443.5 g) of D-citronellal were isolated within 5 days. The yield of D-citronellal was 92% based on the cis-citral used.

EXAMPLE 3

With the same base settings, the hydrogenation reactor was charged with 60.3 l (STP)/h of $H_2$ with 265 ppm of CO, which established a CO value of about 1300 ppm in the offgas of the hydrogenation catalyst. In this way, 2.87 mol (441.9 g) of D-citronellal were isolated within 5 days. The yield of D-citronellal was 90% based on the cis-citral used.

The invention claimed is:
1. A process for preparing optically active carbonyl compounds by asymmetrically hydrogenating α,β-unsaturated carbonyl compounds in the presence of optically active transition metal catalysts which are soluble in the reaction mixture and have at least one carbon monoxide ligand, the optically active catalyst which has at least one carbon monoxide ligand and is to be used in each case being prepared by pretreating a catalyst precursor with a gas mixture comprising carbon monoxide and hydrogen and the asymmetric hydrogenation being performed in the presence of carbon monoxide supplied additionally to the reaction mixture, which comprises the consecutive steps of
a) performing the pretreatment of the catalyst precursor with a gas mixture comprising from 30 to 70% by volume of carbon monoxide, from 30 to 70% by volume of hydrogen and from 0 to 5% by volume of further gases, the proportions by volume mentioned adding up to 100% by volume, at a pressure of from 50 to 90 bar, b) removing excess carbon monoxide from the catalyst thus obtained before use in the asymmetric hydrogenation by decompressing the catalyst pretreated in step a) to a pressure in the range of from 1 to 3 bar, and c) performing the asymmetric hydrogenation in the presence of hydrogen with a carbon monoxide content of from 100 to 1200 ppm, wherein said process is performed continuously, and wherein the reaction product is removed from the reaction mixture and the remaining catalyst is reused after preformation according to step a).

2. The process according to claim 1 for preparing optically active carbonyl compounds of the formula (I)

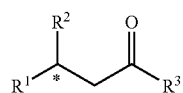

(I)

where the $R^1$, $R^2$ radicals are each an unbranched, branched or cyclic alkyl radical which has from 1 to 25 carbon atoms and may optionally bear one or more ethylenic double bonds and/or one or more identical or different substituents selected from the group of the substituents $OR^4$, $NR^5R^6$, halogen, $C_6$-$C_{10}$-aryl and $C_3$-$C_9$-hetaryl, and which, together with $R^3$, may form a 5- to 25-membered ring, with the proviso that $R^1$ and $R^2$ are different, the $R^3$ radical is hydrogen or an unbranched, branched or cyclic alkyl radical which has from 1 to 25 carbon atoms and may optionally bear one or more ethylenic double bonds and/or one or more identical or different substituents selected from the group of the substituents $OR^4$, $NR^5R^6$, halogen, $C_6$-$C_{10}$-aryl and $C_3$-$C_9$-hetaryl, or $OR^7$ or $NR^8R^9$, where $R^4$, $R^5$, $R^6$ are each independently hydrogen, $C_1$-$C_6$-alkyl, $C_6$-$C_{10}$-aryl, $C_7$-$C_{12}$-aralkyl or $C_7$-$C_{12}$-alkylaryl and $R^5$ and $R^6$ together may also be an alkylene chain which has from 2 to 5 carbon atoms and may be interrupted by N or O and $R^7$ is an unbranched, branched or cyclic alkyl radical which has from 1 to 25 carbon atoms and may optionally bear one or more ethylenic double bonds and one or more identical or different substituents selected from the group of the substituents $OR^4$, $NR^5R^6$, halogen, $C_6$-$C_{10}$-aryl and $C_3$-$C_9$-hetaryl, and, together with $R^1$ or $R^2$, may form a 5- to 25-membered ring and $R^8$ is an unbranched, branched or cyclic alkyl radical which has from 1 to 25 carbon atoms and may optionally bear one or more ethylenic double bonds and one or more identical or different substituents selected from the group of the substituents $OR^4$, $NR^5R^6$, halogen, $C_4$-$C_{10}$-aryl and $C_3$-$C_9$-hetaryl, and, together with $R^1$, $R^2$ or $R^9$, may form a 5- to 25-membered ring and $R^9$ is hydrogen, $C_1$-$C_6$-alkyl, $C_6$-$C_{10}$-aryl, $C_7$-$C_{12}$-aralkyl or $C_7$-$C_{12}$-alkylaryl, or, together with $R^8$, may form a 5- to 25-membered ring and

* designates an asymmetric carbon atom, by asymmetrically hydrogenating α,β-unsaturated aldehydes or ketones of the formula (II)

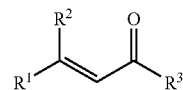

(II)

where the $R^1$ to $R^3$ radicals are each as defined above.

3. The process according to claim 1 for preparing optically active aldehydes or ketones by asymmetrically hydrogenating α,β-unsaturated aldehydes or ketones.

4. The process according to claim 3 for preparing optically active aldehydes of the formula (III)

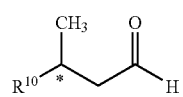

(III)

where $R^{10}$ is an unbranched or branched alkyl radical which has from 2 to 25 carbon atoms and may optionally have from 1 to 5 ethylenic double bonds and

* designates an asymmetric carbon atom, by asymmetrically hydrogenating α,β-unsaturated aldehydes of the formula (IV) or (V)

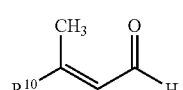

(IV)

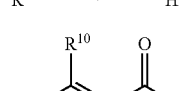

(V)

where the $R^{10}$ radical is as defined above.

5. The process according to claim 4 for preparing optically active citronellal of the formula (VI)

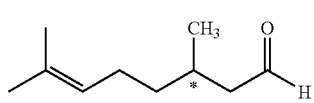

(VI)

by asymmetrically hydrogenating neral of the formula (VII) or geranial of the formula (VIII)

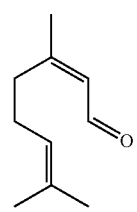

(VII)

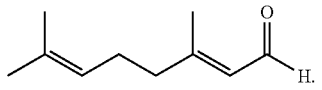

(VIII)

6. The process according to claim 5 for preparing D-citronellal by asymmetrically hydrogenating neral.

7. The process according to claim 1, wherein a transition metal catalyst precursor which is obtainable by reacting at least one transition metal compound which is soluble in the reaction mixture and has an optically active ligand which has at least one phosphorus and/or arsenic atom is used.

8. The process according to claim 7, wherein the optically active ligand used is a compound of the general formula (IX), (X) or (XI)

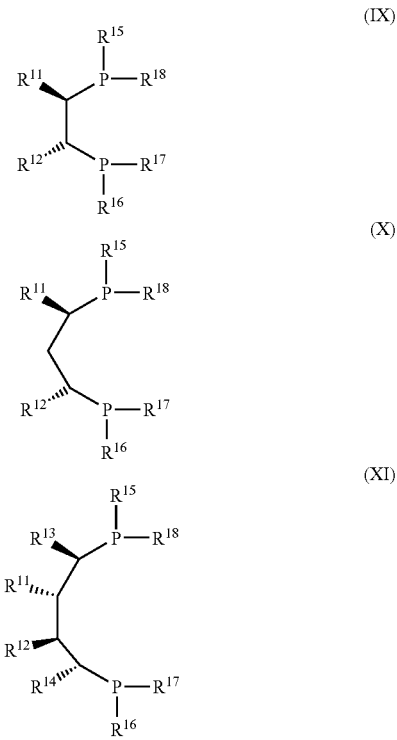

in which $R^{11}, R^{12}$: are each independently an unbranched, branched or cyclic alkyl radical which has from 1 to 20 carbon atoms and may optionally bear one or more, generally from 1 to about 4, ethylenic double bonds and/or one or more, generally from 1 to about 4, identical or different substituents selected from the group of the substituents $OR^{19}$, $NR^{20}R^{21}$, halogen, $C_6$-$C_{10}$-aryl and $C_3$-$C_9$-hetaryl, and $R^{11}$ and $R^{12}$ together may form a 4- to 20-membered ring which may include one or more, generally 1 or 2, oxygen atoms, and $R^{13}$, $R^{14}$: are each independently hydrogen or straight-chain or branched $C_1$- to $C_4$-alkyl and $R^{15}$, $R^{16}$, $R^{17}$, $R^{18}$: are each $C_6$- to $C_{10}$-aryl which may optionally bear one or more, generally from 1 to 8, preferably from 1 to 4, substituents selected from the group of the substituents $C_1$- to $C_4$-alkyl, $C_6$- to $C_{10}$-aryl, $C_1$- to $C_4$-alkoxy and amino, and $R^{19}$, $R^{20}$, $R^{21}$: are each independently hydrogen, $C_1$-$C_4$-alkyl, $C_6$-$C_{10}$-aryl, $C_7$-$C_{12}$-aralkyl or $C_7$-$C_{12}$-alkylaryl, where $R^{20}, R^{21}$: together may also be an alkylene chain which has from 2 to 5 carbon atoms and may be interrupted by N or O.

9. The process according to claim 7, wherein the transition metal compound is a compound of a metal of transition group VIII of the Periodic Table of the Elements.

10. The process according to claim 7, wherein a compound of the metals rhodium or iridium is used.

11. The process according to claim 7, wherein the transition metal compound is a rhodium compound.

12. The process according to claim 7, wherein an optically active ligand of the formula (IX) where the $R^{11}$, $R^{12}$ and $R^{15}$ to $R^{18}$ radicals are each as defined above is used.

13. The process according to claim 7, that the optically active ligand used is the ligand of the formula (1) (S,S-chiraphos) or ent-(1) (R,R-chiraphos)

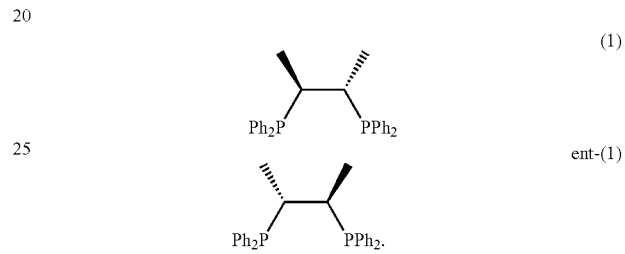

14. The process according to claim 1, wherein the asymmetric hydrogenation is performed at a pressure of from 10 to 100 bar.

15. The process according to claim 1, wherein the pretreatment of the catalyst precursor in step a) is performed with a gas mixture comprising from 40 to 60% by volume of carbon monoxide, from 60 to 40% by volume of hydrogen and from 0 to 5% by volume of further gases, where the proportions by volume mentioned add up to 100% by volume.

16. The process according to claim 1, wherein the asymmetric hydrogenation in step c) is performed in the presence of hydrogen having a carbon monoxide content of from 400 to 800 ppm.

17. The process according to claim 1, wherein the asymmetric hydrogenation in step c) is performed in a gas circulation reactor.

18. The process according to claim 17, wherein the α,β-unsaturated carbonyl compound to be converted and the hydrogen are introduced into the gas circulation reactor by means of a two-substance nozzle.

19. A process for preparing optically active menthol, comprising the steps of
   i) preparing optically active citronellal according to claim 1,
   ii) cyclizing the optically active citronellal thus prepared to optically active isopulegol in the presence of a Lewis acid and
   iii) hydrogenating the optically active isopulegol thus prepared to optically active menthol.

\* \* \* \* \*